(12) United States Patent
Bae et al.

(10) Patent No.: US 9,724,334 B1
(45) Date of Patent: Aug. 8, 2017

(54) METHOD FOR TREATING A NEURODEGENERATIVE DISEASE OR DEPRESSION COMPRISING ADMINISTERING DERIVATIVES OF 2-AMINO-2-(1-DODECYL-1H-1,2,3-TRIAZOL-4-YL)PROPANE-1,3-DIOL

(71) Applicant: Kyungpook National University Industry-Academic Cooperation Foundation, Daegu (KR)

(72) Inventors: Jae-Sung Bae, Daegu (KR); Hee Kyung Jin, Daegu (KR); Min Hee Park, Gyeongsangbuk-do (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 0 days.

(21) Appl. No.: 15/417,315

(22) Filed: Jan. 27, 2017

(30) Foreign Application Priority Data

Sep. 30, 2016 (KR) .......................... 10-2016-0126750

(51) Int. Cl.
 *A61K 31/4192* (2006.01)
 *C07D 249/04* (2006.01)
(52) U.S. Cl.
 CPC ........ *A61K 31/4192* (2013.01); *C07D 249/04* (2013.01)

(58) Field of Classification Search
 CPC .......................... A61K 31/4192; C07D 249/04
 See application file for complete search history.

(56) References Cited

FOREIGN PATENT DOCUMENTS

KR  10-1521117  5/2015

OTHER PUBLICATIONS

Beckmann et al., "Inhibition of acid sphingomyelinase by tricyclic antidepressants and analogons," Frontiers in Physiology, vol. 5, No. 331, pp. 1-14 (Sep. 2014).
Dawson et al., "Gilenya (FTY720) inhibits acid sphingomyelinase by a mechanism similar to tricyclic antidepressants," Biochem and Biophysical Research Comm, vol. 404, pp. 321-323 (2011).
Gulbins et al, "Acid sphingomyelinase—ceramide system mediates effects of antidepressant drugs," Nature Medicine, vol. 19, No. 7, (9 pages), pp. 934-938; 3214 (Jul. 2013).
Zoicas et al., "Role of Acid Sphingomyelinase in the Regulation of Social Behavior and Memory," PLOS One, vol. 11, No. 9, pp. 1-11 (Sep. 6, 2016).

*Primary Examiner* — Robert Havlin
(74) *Attorney, Agent, or Firm* — Jenkins, Wilson, Taylor & Hunt

(57) ABSTRACT

A method for treating a neurodegenerative disease and depression, the method comprising administering to a subject in need thereof an effective amount of a composition comprising derivatives of 2-amino-2-(1-dodecyl-1H-1,2,3-triazol-4-yl)propane-1,3-diol as an active ingredient.

3 Claims, 16 Drawing Sheets

*P < 0.05

*P < 0.05 compared to WT
P < 0.05 compared to AD/control
n = 7-8

*P < 0.05 compared to WT
P < 0.05 compared to AD/control
n = 7-8

METHOD FOR TREATING A NEURODEGENERATIVE DISEASE OR DEPRESSION COMPRISING ADMINISTERING DERIVATIVES OF 2-AMINO-2-(1-DODECYL-1H-1,2,3-TRIAZOL-4-YL)PROPANE-1,3-DIOL

CROSS-REFERENCE TO RELATED APPLICATIONS

The present application claims a priority from Korean Patent Application No. 10-2016-0126750 filed on Sep. 30, 2016. The disclosures of the said application are incorporated by reference as if fully set forth herein.

BACKGROUND

Field

Exemplary embodiments relate to a method for treating a neurodegenerative disease or depression, the method comprising administering to a subject in need thereof an effective amount of derivatives of 2-amino-2-(1-dodecyl-1H-1,2,3-triazol-4-yl)propane-1,3-diol. More particularly, exemplary embodiments relate to a method for treating a neurodegenerative disease or depression, the method comprising administering to a subject in need thereof an effective amount of derivatives of 2-amino-2-(1-dodecyl-1H-1,2,3-triazol-4-yl)propane-1,3-diol which possess an effect of inhibiting ASM activity.

Discussion of the Background

Sphingolipid metabolism controls normal cell signaling, and abnormal changes in sphingolipid metabolism affect a variety of neurodegenerative diseases including Alzheimer's disease. Meanwhile, ASM (acid sphingomyelinase), an enzyme that regulates sphingolipid metabolism, is a protein which is expressed in almost all kinds of cells and plays an important role in sphingolipid metabolism and cell membrane turnover.

According to previous studies by the present inventors, it was found that the activity of ASM is increased in various neurodegenerative diseases including Alzheimer's disease, and ASM inhibition can thus be a new approach for treating neurodegenerative diseases. It was recently reported that the activity of ASM is increased in neurological diseases such as depression, and that the suppression of ASM is effective in ameliorating the severity of depression (Nature medicine, 2013 Jul. 19(7):934-938, PLoS One 2016 Sep. 6; 11(9): e0162498). Therefore, the development of ASM inhibitors is promising as a useful method for treating various ASM-increased diseases including neurodegenerative diseases.

By the way, to date, some inhibitors which may indirectly inhibit ASM have been identified, while no direct ASM inhibitors have been developed. First, tricyclic antidepressants (e.g., amitriptyline (AMI), desipramine, imipramine, etc.), which are most commonly used as indirect inhibitors of ASM, are used in clinical practice as antidepressant drugs. Although not initially developed as ASM inhibitors, various studies have demonstrated that these drugs exhibit ASM inhibitory effects. The main mode of action of tricyclic antidepressants is the increase of neurotransmitter activity by inhibiting the reabsorption of neurotransmitters in neurons, with the side effect of suppressing ASM. However, in the case of tricyclic antidepressant drugs, it is necessary to develop a novel inhibitor compound of ASM activity since it acts on the nervous system and neurons and may cause adverse side effects such as blurring, increased light sensitivity, and vomiting.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide 2-amino-2-(1-dodecyl-1H-1,2,3-triazol-4-yl) propane-1,3-diol derivatives capable of significantly inhibiting ASM activity and treating a neurodegenerative disease and depression.

Additional aspects will be set forth in the detailed description which follows, and, in part, will be apparent from the disclosure, or may be learned by practice of the inventive concept.

An exemplary embodiment discloses a pharmaceutical composition for treating a neurodegenerative disease or depression, the composition comprising a compound of the following Chemical Formula 1 or a pharmaceutically acceptable salt thereof as an active ingredient:

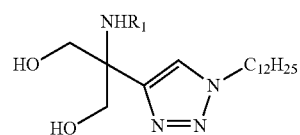

[Chemical Formula 1]

wherein $R_1$ is hydrogen or an acetyl group.

An exemplary embodiment also discloses a food composition for improving a neurodegenerative disease or depression, the composition comprising a compound of the following Chemical Formula 1 or a pharmaceutically acceptable salt thereof as an active ingredient:

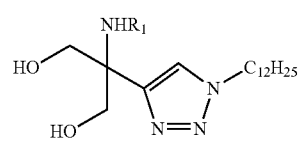

[Chemical Formula 1]

wherein $R_1$ is hydrogen or an acetyl group.

An exemplary embodiment further discloses a method for treating a neurodegenerative disease or depression, the method comprising administering to a subject in need thereof an effective amount of a compound of the following Chemical Formula 1 or a pharmaceutically acceptable salt thereof:

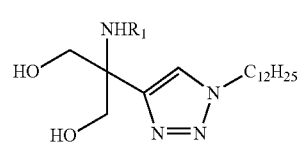

[Chemical Formula 1]

wherein $R_1$ is hydrogen or an acetyl group.

BRIEF DESCRIPTION OF THE DRAWINGS

FIG. 6A is a graph showing the experimental results of evaluating learning and memory through the Morris Watermaze test on wild type mice (n=8), APP/PS1 mice (n=7) in which the ASM inhibitory compound of the Chemical Formula 2 was fed through drinking water, APP/PS1 mice (n=8) in which AMI was fed through drinking water, and APP/PS1 mice (n=8) in which none was fed.

FIG. 6B shows the time spent by the mice in the target platform on the $11^{th}$ day of testing.

FIG. 6C shows the number of times each mouse entered the target area in the target platform on the $11^{th}$ day of testing.

FIG. 6D shows the results of the contextual and tone tasks during the fear conditioning test.

FIG. 7A and FIG. 7B are the results of measuring the time spent by the mice on the wall (A) and the center (B) during the open field test.

FIG. 7C shows the ratio of the center portion during the open field test.

FIG. 7D shows the movement path of the mice during the open field test.

FIG. 7E and FIG. 7F are the results of measuring the time spent by the mice in the dark place (E) and in the bright place (F) during the dark & light test.

FIG. 7G shows the number of times the mice made a round trip between the dark place and bright place during the dark & light test.

FIG. 7H shows the result of measuring the time taken for the first move of the mice from the dark place to the bright place during the dark & light test.

FIG. 7I shows the movement path of the mice during the dark & light test.

FIG. 8A shows the results (GFAP) of immunofluorescent images (left) and its quantification (right) of astrocytes in the cerebral cortex of wild type mice (WT) and APP/PS1 mice that were not fed or fed with the novel ASM inhibitory compound of the Chemical Formula 2 through drinking water, respectively.

FIG. 8B shows the results of evaluating the mRNA expression levels of inflammatory markers (TNF-α, IL-1β, IL-6) in the cerebral cortex of wild type mice (WT) and APP/PS1 mice that were not fed or fed with the novel ASM inhibitory compound of the Chemical Formula 2 through drinking water, respectively.

DETAILED DESCRIPTION OF THE ILLUSTRATED EMBODIMENTS

Figure 1:
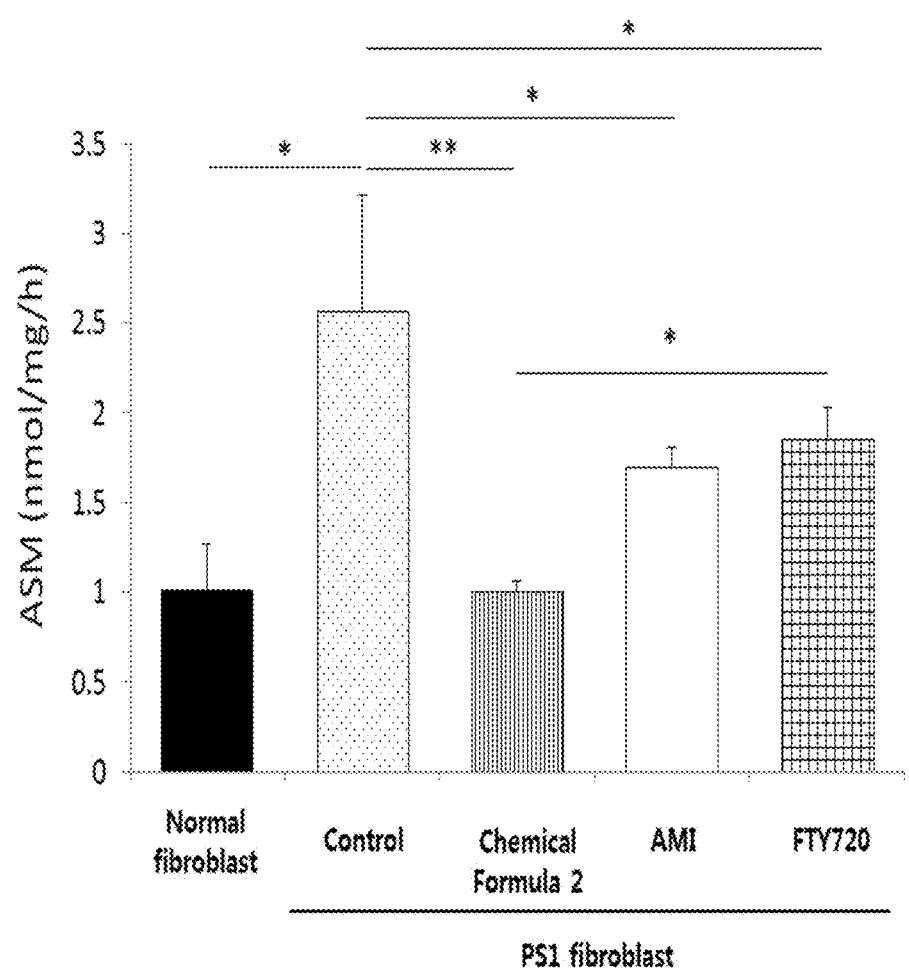
FIG. 1 is a graph showing changes in ASM activity after treating the novel ASM inhibitory compound of the Chemical Formula 2, AMI and FTY720 in fibroblasts of Alzheimer's patients with increased ASM activity.

Hereinafter, the present invention will be described in more detail.

The present invention provides a pharmaceutical composition for treating a neurodegenerative disease or depression, the composition comprising a compound of the following Chemical Formula 1 or a pharmaceutically acceptable salt thereof as an active ingredient:

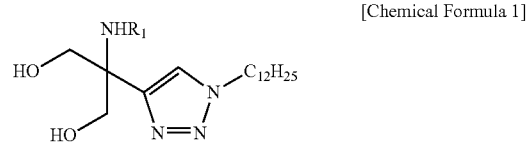

[Chemical Formula 1]

wherein $R_1$ is hydrogen or an acetyl group.

The expression of ASM is significantly elevated in the brains of patients with neurodegenerative diseases including Alzheimer's disease. It has been reported that the suppression of the expression of overexpressed ASM or suppression of ASM activity inhibits the accumulation of amyloid-beta (Aβ) and improves learning and memory, resulting in the effective treatment of neurodegenerative diseases (Korea Patent No. 10-1521117). Recently, it was also found that the activity of ASM is increased in neurological diseases such as depression, and that the suppression of ASM leads to the amelioration of depression (Nature medicine. 2013 Jul. 19(7):934-938, PLoS One. 2016 Se[6; 11(9):e0162498). Therefore, a substance capable of inhibiting the expression or activity of ASM can be developed as a useful therapeutic agent for treating such diseases as neurodegenerative diseases and depression.

According to one embodiment of the present invention, it is verified that the compound of the Chemical Formula 1 has an excellent activity in inhibiting ASM, reducing Aβ plaques in Alzheimer's brain environment, recovering the damages by autophagy, decreasing nerve inflammation and the like, and thus can be used as a preventive or therapeutic agent for a neurodegenerative disease (including Alzheimer's disease) and depression.

As used herein, the neurodegenerative disease is not limited to, but is selected from the group consisting of Alzheimer's disease, Parkinson's disease, progressive supranuclear palsy, multiple system atrophy, olivopontocerebellar atrophy (OPCA), Shy-Drager syndrome, striatonigral degeneration, Huntington disease, amyotrophic lateral sclerosis (ALS), essential tremor, cortico-basal ganglionic degeneration, diffuse Lewy body disease, Parkinson-ALS-dementia complex of Guam, Pick's disease, cerebral ischemia and cerebral infarction.

The present invention includes not only the compounds represented by the above-mentioned Chemical Formula 1, but also pharmaceutically acceptable salts thereof, possible solvates, hydrates, racemates or stereoisomers thereof.

The compound represented by the Chemical Formula 1 of the present invention can be used in the form of a pharmaceutically acceptable salt, while an acid addition salt formed by a pharmaceutically acceptable free acid is useful as the form of its salt. Acid addition salts include those derived from inorganic acids such as hydrochloric acid, nitric acid, phosphoric acid, sulfuric acid, hydrobromic acid, hydroiodic acid, nitrous acid or phosphorous acid; and those derived from non-toxic organic acids such as aliphatic mono- and dicarboxylates, phenyl-substituted alkanoates, hydroxyalkanoates and alkanedioate, aromatic acid, aliphatic and aromatic sulfonic acids. Such pharmaceutically non-toxic salts include, but are not limited to, sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phtalate, terephtalate, benzenesulfonate, toluenesulfonate, chlorobenzene sulfonate, xylenesulfonate, phenylacetate, phenylpropionate, phenylbutyrate, citrate, lactate, hydroxybutyrate, glycolate, maleate, tartrate, methanesulfonate, propanesulfonate, naphthalene-1-sulfonate, naphthalene-2-sulfonate or mandelate.

The acid addition salt according to the present invention can be obtained by conventional methods, for example, by dissolving the compound represented by the Chemical Formula 1 in an excess amount of an acid aqueous solution, and then precipitating the resulting salt with a water-miscible organic solvent such as methanol, ethanol, acetone or acetonitrile. The acid addition salt may be prepared by evaporating and drying the solvent or the excess acid from the mixture or by suction filtration of the precipitated salt.

In addition, bases can be used to make pharmaceutically acceptable metal salts. The alkali metal or alkaline earth metal salt is obtained, for example, by dissolving the compound in an excess amount of an alkali metal hydroxide or alkaline earth metal hydroxide solution, filtering the insoluble compound salt, and evaporating and drying the filtrate. At this time, for the purpose of preparing the metal salt, it is suitable to produce sodium, potassium or calcium salt. In addition, the corresponding silver salt is obtained by reacting an alkali metal or alkaline earth metal salt with a suitable salt (for example, silver nitrate).

The pharmaceutical composition according to the present invention may be formulated into a suitable form comprising the compound of the Chemical Formula 1 or a pharmaceutically acceptable salt thereof alone or together with a pharmaceutically acceptable carrier, and may further contain an excipient or diluent. As used herein, the term "pharmaceutically acceptable" refers to a non-toxic composition that is physiologically acceptable and does not normally cause an allergic reaction such as gastrointestinal disorder, dizziness, or the like when administered to humans.

The pharmaceutically acceptable carrier may further include, for example, a carrier for oral administration or a carrier for parenteral administration. Carriers for oral administration may include lactose, starch, cellulose derivatives, magnesium stearate, stearic acid, and the like. It may also contain various drug delivery materials used for oral administration of peptide preparations. In addition, the carrier for parenteral administration may include water, a suitable oil, a saline solution, an aqueous glucose and a glycol, and may further contain a stabilizer and a preservative. Suitable stabilizers include antioxidants such as sodium hydrogen sulfite, sodium sulfite and ascorbic acid. Suitable preservatives include benzalkonium chloride, methyl- or propylparaben and chlorobutanol. The pharmaceutical composition of the present invention may further contain a lubricant, a wetting agent, a sweetener, a flavoring agent, an emulsifying agent, a suspending agent and the like, in addition to the above components. Other pharmaceutically acceptable carriers and preparations can be found in Remington's Pharmaceutical Sciences (19th ed., Mack Publishing Company, Easton, Pa., 1995).

The composition of the present invention can be administered to mammals including humans by any method. For example, it can be administered orally or parenterally. Parenteral administration methods include, but are not limited to, intravenous, intramuscular, intraarterial, intramedullary, intrathecal, intracardiac, transdermal, subcutaneous, intraperitoneal, intranasal, enteral, topical, sublingual or rectal administration.

The pharmaceutical composition of the present invention may be formulated into oral or parenteral dosage forms according to the administration routes as described above.

In the case of a preparation for oral administration, the composition of the present invention may be formulated into powder, granule, tablet, pill, sugar-coated tablet, capsule, liquid, gel, syrup, slurry, suspension or the like by methods known in the art. For example, an oral preparation can be obtained by combining the active ingredient with a solid excipient, then pulverizing it, adding suitable auxiliaries, and then processing the mixture into granules to obtain tablets or sugar-coated tablets. Examples of suitable excipients include sugars such as lactose, dextrose, sucrose, sorbitol, mannitol, xylitol, erythritol and maltitol; and starches such as corn starch, wheat starch, rice starch and potato starch; cellulose derivatives such as cellulose, methyl cellulose, sodium carboxymethyl cellulose and hydroxypropylmethyl cellulose; gelatin, polyvinylpyrrolidone, and the like as a filler. In addition, crosslinked polyvinylpyrrolidone, agar, alginic acid or sodium alginate may optionally be added as a disintegrant. Furthermore, the pharmaceutical composition of the present invention may further comprise an anti-coagulant, a lubricant, a wetting agent, a flavoring agent, an emulsifying agent and an antiseptic agent.

The preparation for parenteral administration may be formulated in the form of injections, creams, lotions, topical ointments, oils, moisturizers, gels, aerosols and nasal inhalers by methods known in the art. These formulations are described in Remington's Pharmaceutical Science (19th ed., Mack Publishing Company, Easton, Pa., 1995), which is a commonly known formulary for all pharmaceutical chemistries.

The total effective amount of the composition of the present invention may be administered to a patient in a single dose, or administered by a fractionated treatment protocol over a prolonged period of time in multiple doses. The pharmaceutical composition of the present invention may vary in the content of its active ingredient depending on the severity of disease. Preferably, the total preferred dose of the pharmaceutical composition of the present invention may be in the range of about 0.01 µg to 10,000 mg, and most preferably in the range of 0.1 µg to 500 mg, per kilogram of patient body weight per day. However, the dosage of the pharmaceutical composition may be determined depending on various factors such as the formulation method, administration route, and the number of treatment as well as the patient's age, weight, health condition, sex, severity of disease, diet and excretion rate. Those skilled in the art will be able to determine the appropriate effective dose of the composition of the present invention in view of the above mentioned factors. The pharmaceutical composition according to the present invention is not particularly limited in terms of the formulation, administration route, and administration method as long as the effect of the present invention is exhibited.

The present invention provides a food composition for improving neurodegenerative diseases or depression comprising, as an active ingredient, a compound represented by the following Chemical Formula 1 or a pharmaceutically acceptable salt thereof:

[Chemical Formula 1]

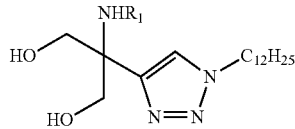

wherein $R_1$ is hydrogen or an acetyl group.

The food composition according to the present invention includes all forms such as functional food, nutritional supplement, health food and food additives. These types can be prepared in various forms according to conventional methods known in the art.

For example, as a health food, the food composition itself of the present invention may be prepared in the form of tea, juice or drink, and may be ingested in a drinkable form, or in a granulated, encapsulated or powdered form. In addition, the food composition of the present invention may be prepared in the form of a composition by mixing with known substances or active ingredients which are known to be effective for preventing or treating neurodegenerative diseases or depression.

Functional foods may be prepared by containing the food composition of the present invention in beverages (including alcoholic beverages), fruits and their processed foods (such as canned fruits, bottled fruits, jam, marmalade), fish, meat and processed foods (such as ham, sausage, corn beef), breads and noodles (such as udon, buckwheat noodles, ramen, spaghetti, macaroni), juice, various drinks, cookies, taffy, milk products (such as butter and cheese), edible vegetable oil, margarine, vegetable protein, retort food, frozen food, various seasonings (such as soybean paste, soy sauce, sauce) and the like.

The preferable content of the food composition according to the present invention is, without limitation, preferably 0.01 to 50% by weight of the total weight of the final food. In order to use the food composition of the present invention in the form of a food additive, it may be used in the form of powder or concentrate.

Further, the present invention provides a method for treating a neurodegenerative disease or depression, the method comprising administering to a subject in need thereof an effective amount of a compound of the following Chemical Formula 1 or a pharmaceutically acceptable salt thereof:

[Chemical Formula 1]

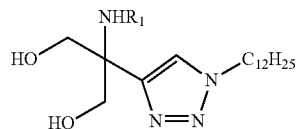

wherein $R_1$ is hydrogen or an acetyl group.

As used herein, the term "effective amount" refers to an amount that, when administered to a subject, leads to the effect of improvement, treatment, prevention, detection or diagnosis of a neurodegenerative disease and depression. The term "subject" refers to an animal, preferably a mammal which especially includes a human, while including animal-derived cells, tissues, organs and the like. The subject may be a patient in need of the above mentioned effect.

As used herein, the term "treating" broadly refers to the improvement of diseases or disorders associated with the neurodegenerative disease and depression, or the amelioration of symptoms derived from diseases or disorders associated with the neurodegenerative disease and depression, while including, without limitation, curing, substantially preventing, and improving said diseases or disorders; and relieving, curing or preventing one or more of the symptoms resulting from said diseases or disorders associated with the neurodegenerative diseases and depression.

The novel ASM inhibitory compound of the present invention possesses an ASM inhibitory effect superior to that of the conventional ASM inhibitors and exerts a therapeutic effect such as reduction of Aβ plaques in Alzheimer's brain environment, recovery from the damages by autophagy, and alleviation of nerve inflammation, leading to its useful applicability for developing an agent for preventing or treating a neurodegenerative disease including Alzheimer's disease. In addition, ASM inhibitory compounds of the Chemical Formula 1 of the present invention can be usefully used as an agent for preventing or treating neurological diseases including depression, as indicated in the prior reports that inhibition of ASM is effective for relieving depression.

However, the following examples are merely for illustrating the present invention and are not intended to limit the scope of the present invention.

EXPERIMENTAL METHODS

Experimental Materials

Herein, the ASM inhibitory effect of 2-amino-2-(1-dodecyl-1H-1,2,3-triazol-4-yl)propane-1,3-diol represented by the Chemical Formula 2, AMI and FTY720 was evaluated, respectively.

[Chemical Formula 2]

The compound of the Chemical Formula 2 was prepared and synthesized by the previously disclosed references (See Synthesis of heterocyclic analogues of FTY720 using Copper (I)-catalyzed [3+2] cycloaddition. 2012. Seoul National University Graduate School, Source: 82SNU INST). AMI and FTY720 used as positive controls were purchased from Sigma-Aldrich, respectively.

1. Mouse

IACUC (Kyungpook National University Institutional Animal Care and Use Committee) approved the present mouse experiment. A transgenic mouse line overexpressing APPswe (hAPP695swe) or PS1 (preseniline-1M146V) was used based on C57BL/6 mouse (Charles River, UK) (hereinafter, APP mouse: APPswe-overexpressing mouse, PS1 mouse: presenilin-1M146V overexpressing mouse; GlaxoSmithKline).

Figure 3:
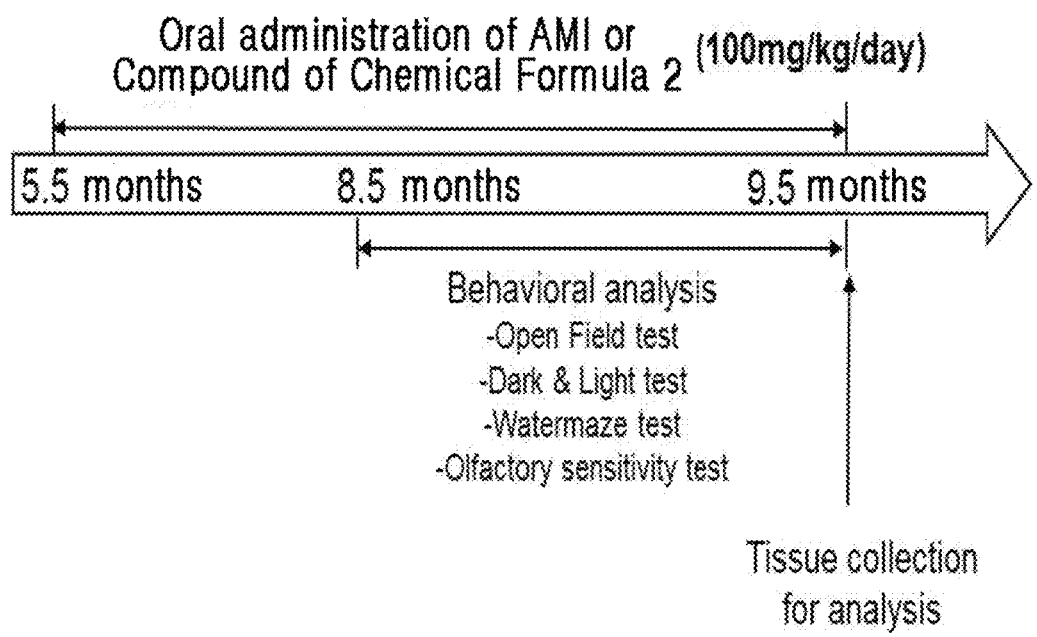
FIG. 3 is a diagram showing the outline of an experiment carried out in order to examine the effect of the ASM inhibitory compound of the Chemical Formula 2 on Alzheimer's disease.

To confirm the therapeutic effect of the novel ASM inhibitory compounds, the novel ASM inhibitory compound or AMI were fed via drinking water at a dose of 100 mg/kg/day to mice at 5.5 months of age. Three months after the feeding, behavioral analysis on the mice was performed, followed by sampling of mouse brain tissues (FIG. 3).

2. Immunofluorescence

After fixing the cerebrum and hippocampus of the test mice, 0.5% thioflavin S (Sigma-Aldrich), anti-20G10 antibodies (Mouse, 1:1000) against Aβ, 42 and anti-G30 antibodies (rabbit, 1:1000) against Aβ, 40, anti-GFAP antibodies (rabbit, 1:500, DAKO) were cultured together. The above sites were analyzed using a laser scanning confocal microscope equipped with Fluoview SV1000 imaging software (Olympus FV1000, Japan) or an Olympus BX51 microscope. Percentage of area of stained area to total tissue area was quantified and analyzed using Metamorph software (Molecular Devices).

3. Real-Time Quantitative PCR

Real-time quantitative PCR was used to measure the expression levels of inflammatory cytokines (TNF-α, IL-1b, and IL-6). Total RNAs were extracted from brain tissues using RNeasy Plus mini kit (Qiagen, Korea, Ltd.), while cDNAs were synthesized from 5 μg of total RNAs using a kit from Clontech (Mountain View, Calif.). Also, using Corbett research RG-6000 real-time PCR instrument, PCR was performed at 95° C. for 10 minutes; 95° C. for 10 seconds; 58° C. for 15 seconds; 72° C. for 20 seconds as one cycle, while real-time quantitative PCR was performed in which 40 cycles were repeated.

Table 1 shows the primers used for the real-time quantitative PCR.

4. Western Blot

Expression of the following genes was analyzed using Western blotting. First, antibodies against LC3, Becklin-1, p62 (All of them were purchased from Cell Signaling Technologies), Cathepsin D (R&D systems) and β-actin (Santa Cruz) were used, while densitometric quantification was performed using ImageJ Software (US National Institutes of Health).

5. Behavioral Experiment

Morris water maze (MWM) and fear conditioning experiments were conducted to identify potential effects on learning and memory. For MWM, the mice were learned the task four times a day for 10 days, followed by the removal of the platform at the $11^{th}$ day and subsequently a probe trial. On the first day of the fear conditioning, the mice were placed in the conditioning chamber and subjected to sound stimulation (10 kHz, 70 dB) and electrical stimulation (0.3 mA, 1s). On the second day, their memory was checked without stimulation in the same conditioning chamber as on the first day. On the third day, memory tests were conducted for fear when only sound stimulation was given in another conditioning chamber. Open field tests and dark & light tests were conducted to assess activity and anxiety. In the open field test, the mice were placed in a square box for 10 minutes to measure their overall activity and time spent wandering the wall and center. In the dark & light test, the mice were placed in a rectangular box composed of a dark box and a bright box for 10 minutes to measure the time spent in each box, the number of round trips, and the time when the mice entered the bright box for the first time.

6. Cell Culture

Human fibroblast cell lines (normal and PS1) were obtained from Coriell Institute and cultured in DMEM containing 15% FBS under the condition of 5% $CO_2$ at 37° C. Subsequently, the cell lines were treated with the ASM inhibitory compound of the Chemical Formula 1, amitriptyline (AMI) and FTY720, followed by measuring the change of ASM activity.

7. Measuring ASM Activity

The concentration levels of ASM were measured as follows. Specifically, a microliter mouse plasma, brain tissue and 3 μl of fibroblast samples were mixed with ASM activity buffer and stored at 37° C. 114 μl of ethanol was added to terminate the hydrolysis reaction, followed by centrifugation. 30 μl of the supernatant was transferred to a glass vial, of which 5 μl was applied to the UPLC system. The ASM concentration levels were quantified by comparison with Bodipy (aminoacetaldehyde) conjugated with sphingomyelin and ceramide. Extraction and quantification of the sphingomyelin and ceramide were performed by extracting lipids from known method samples and resuspending the dried lipid extract in 25 μl of 0.2% Igepal CA-630 (Sigma-Aldrich). Each lipid level was quantified using the UPLC system.

8. Statistical Analysis

For comparison of the two groups, Student's T-test was performed, while the repeated analysis of Tukey's HSD test and distribution test were conducted according to the SAS

TABLE 1

| | | |
|---|---|---|
| mTNF-a | 5'-GAT TAT GGC TCA GGG TCC AA-3' | 5'-GCT CCA GTG AAT TCG GAA AG-3' |
| mIL-1b | 5'-CCC AAG CAA TAC CCA AAG AA-3' | 5'-GCT TGT GCT CTG CTT GTG AG-3' |
| mIL-6 | 5'-CCG GAG AGG AGA CTT CAC AG-3' | 5'-TTG CCA TTG CAC AAC TCT TT-3' |
| mGAPDH | 5'-TGA ATA CGG CTA CAG CAA CA-3' | 5'-AGG CCC CTC CTG TTA TTA TG-3' | statistical package (release 9.1; SAS Institute Inc., Cary, N.C.). p<0.05 was considered statistically significant.

Experimental Results

1. Evaluation on the Change of ASM Activity in Fibroblasts Derived from the Alzheimer's Disease-Afflicted Patient after Treatment of the Novel ASM Inhibitory Compound of the Chemical Formula 2

In order to confirm the ASM inhibitory effect of the compound developed according to the present invention, the ASM inhibitory compound of the Chemical Formula 2, AMI and FTY720 were treated at 10 mM concentration, respectively, in the fibroblasts (PS1 fibroblasts) derived from Alzheimer's disease patients, followed by the measurement of the change of ASM activity. Since being shown to exhibit ASM inhibitory effects by various studies (Biochem Biophys Res Commun. 2011 Jan. 7; 404 (1): 321-323, Front Physiol. 2014 Sep. 2; 5: 331), AMI and FTY720 had not been originally developed as ASM inhibitors but were used as positive controls for the purpose of comparison with the compounds of the present invention.

As a result, it was found that while the ASM activity was significantly increased in the PS1 fibroblasts compared with the normal fibroblasts, this increased ASM activity was markedly reduced by the ASM inhibitory compound of the Chemical Formula 2, AMI and FTY720 treatment, respectively. In particular, it was confirmed that the ASM inhibitory compound of the Chemical Formula 2 was more remarkably effective in inhibiting ASM activity than the other substances (See FIG. 1).

2. Evaluation on the Change of ASM Activity in the APP/PS1 Mice and the Mice Treated with the Novel ASM Inhibitory Compound of the Chemical Formula 2 or AMI Using an experimental animal model APP/PS1 mouse for Alzheimer's disease patients, ASM concentration levels in plasma and brain tissues were measured after administration of AMI, which is the most widely used as an ASM inhibitor, and the novel ASM inhibitory compound of the Chemical Formula 2. The concentration levels of ASM in those mice are shown in FIG. 2.

Figure 2A:
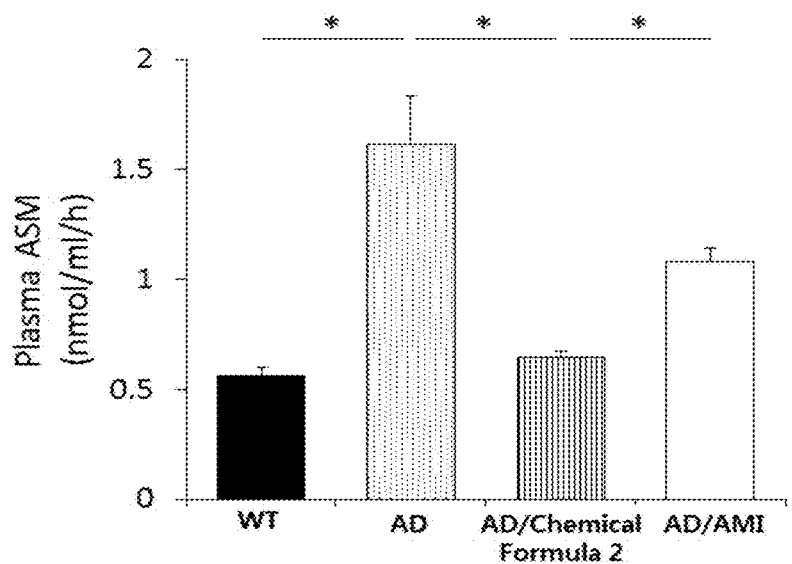
FIGS. 2A and 2B are graphs showing changes in ASM concentration in plasma (FIG. 2A) and brain tissue (FIG. 2B) of APP/PS1 mice after feeding of the ASM inhibitory compound of the Chemical Formula 2 and AMI, respectively, to APP/PS1 mice through drinking water (WT: wild type, AD: Alzheimer's animal model (APP/PS1 mice)).
Figure 2B:
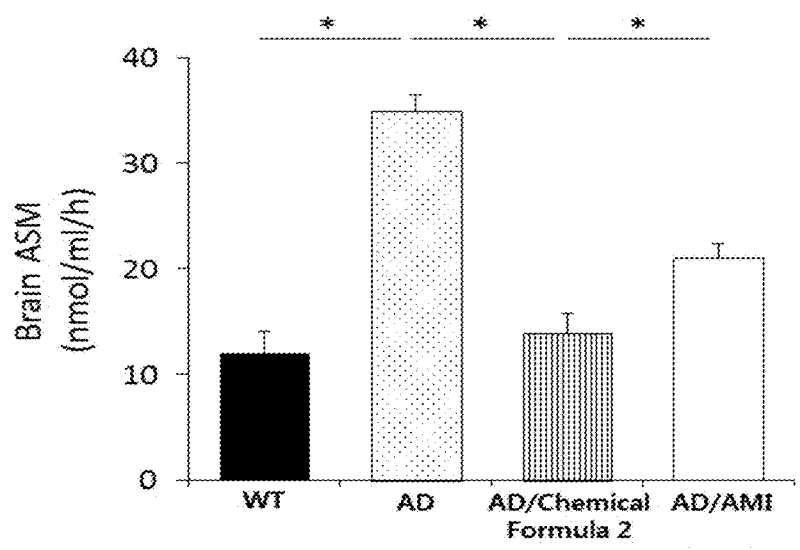

As shown in FIG. 2, in comparison with the level of the ASM concentration in 9.5 month-old APP/PS1 mice's plasma and brain tissues, it was shown that such levels in the mice treated with the novel ASM inhibitory compound of the Chemical Formula 2 or AMI was remarkably low. In particular, it was confirmed that the ASM inhibitory compound of the Chemical Formula 2 was more significantly effective in inhibiting ASM activity than AMI (See FIG. 2).

3. Evaluation on Amyloid-β Deposition in the APP/PS1 Mice and the Mice Treated with the Novel ASM Inhibitory Compound of the Chemical Formula 2 or AMI In order to confirm the effect of the novel ASM inhibitory compound of the Chemical Formula 2 on the lesion of Alzheimer's disease, the ASM inhibitory compound of the Chemical Formula 2 and AMI were administered orally for four months, respectively, as shown in FIG. 3.

To begin with, the profile of Aβ of Alzheimer's disease was identified. First, according to known methods in the art, the cerebral cortex and hippocampus of the mice were stained with thioflavin S (ThioS), confirming the fibrillary amyloid-β deposition. In addition, amyloid-β deposition was confirmed by carrying out the Aβ40 and Aβ42 immunofluorescence.

Figure 4A:
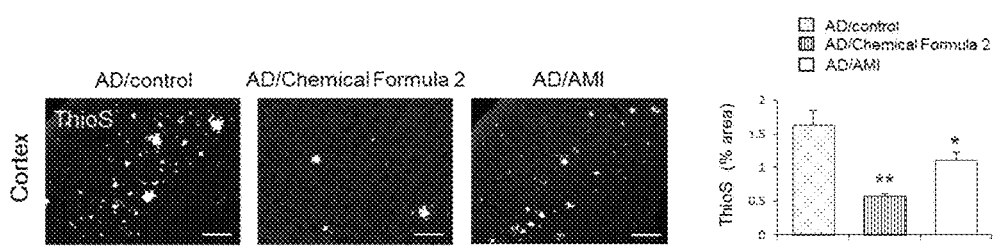
FIGS. 4A and 4B shows the result of immunofluorescent staining of thioflavin S (ThioS, fibrillary amyloid beta plaque) and the quantification of its occupied areas in cerebral cortex (FIG. 4A) and hippocampus (FIG. 4B) of APP/PS1 mice in which the ASM inhibitory compound of the Chemical Formula 2 and AMI were not fed or fed through drinking water, respectively (N=3-4/group) (AD: Alzheimer's animal model (APP/PS1 mice)).
Figure 4B:
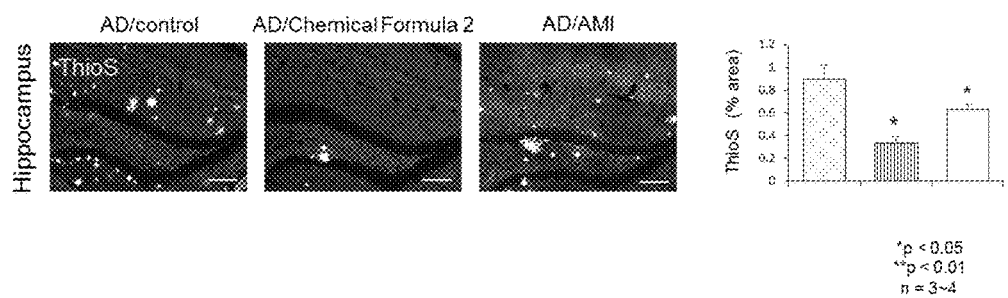
Figure 5A:
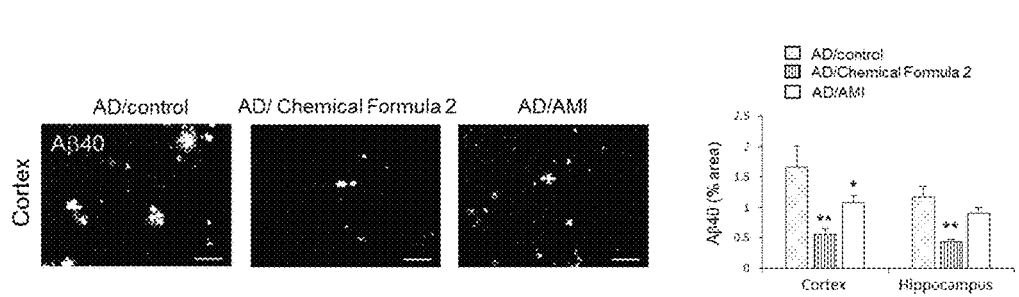
FIGS. 5A and 5B show the result of immunofluorescent staining and quantification of the accumulated Aβ40(FIG. 5A) or Aβ42(FIG. 5B) in the brain tissues of APP/PS1 mice in which the ASM inhibitory compound of the Chemical Formula 2 and AMI were not fed or fed through drinking water, respectively (N=3-4/group) (AD: Alzheimer's animal model (APP/PS1 mice)).
Figure 5B:
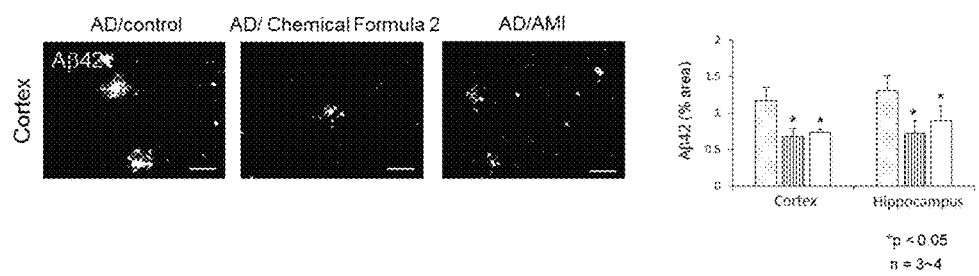

The experimental results showed that fibrillary Aβ deposition (See FIG. 4) and Aβ40 & Aβ42 deposition (See FIG. 5) were significantly lower in the mice treated with the novel ASM inhibitory compound of the Chemical Formula 2 or AMI, in comparison with the APP/PS1 mice. In particular, it was confirmed that amyloid-β deposition in the mice treated with the novel ASM inhibitory compound of the Chemical Formula 2 was more remarkably reduced than the mice treated with AMI (See FIGS. 4 & 5).

4. Evaluation on the Improvement in Learning, Cognition, Activity and Anxiety in APP/PS1 Mice Treated with the Novel ASM Inhibitory Compounds of the Present Invention In order to determine the potential effect of the novel ASM inhibitory compound of the present invention on learning and cognition in the animal models of Alzheimer's disease, the MWM (Morris water maze) and the fear conditioning test were performed, respectively.

Figure 6A:
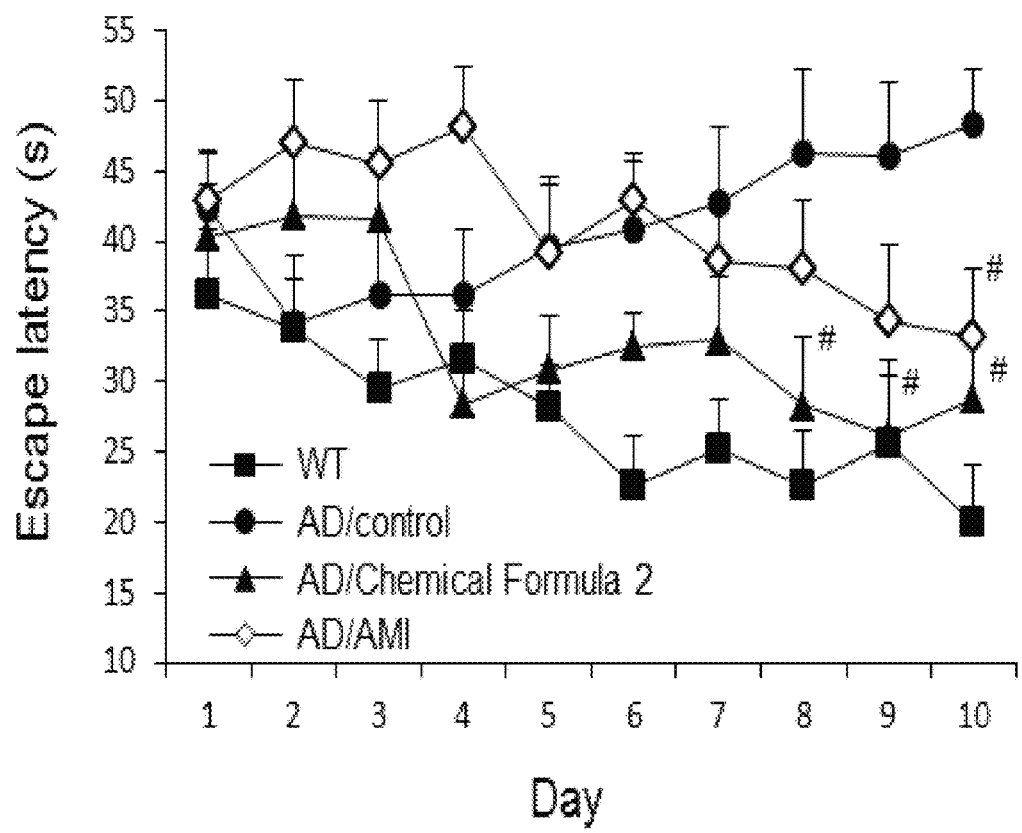
FIGS. 6A to 6D show a result representing the recovery of learning and cognitive function in APP/PS1 mice by feeding the novel ASM inhibitory compound of the Chemical Formula 2 (WT: wild type, AD: Alzheimer's disease animal model (APP/PS1 mouse)).
Figure 6B:
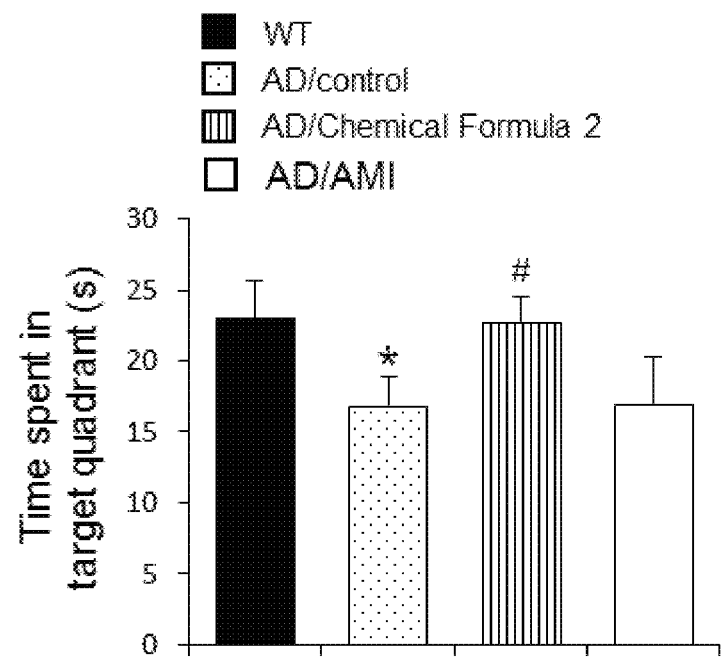
Figure 6C:
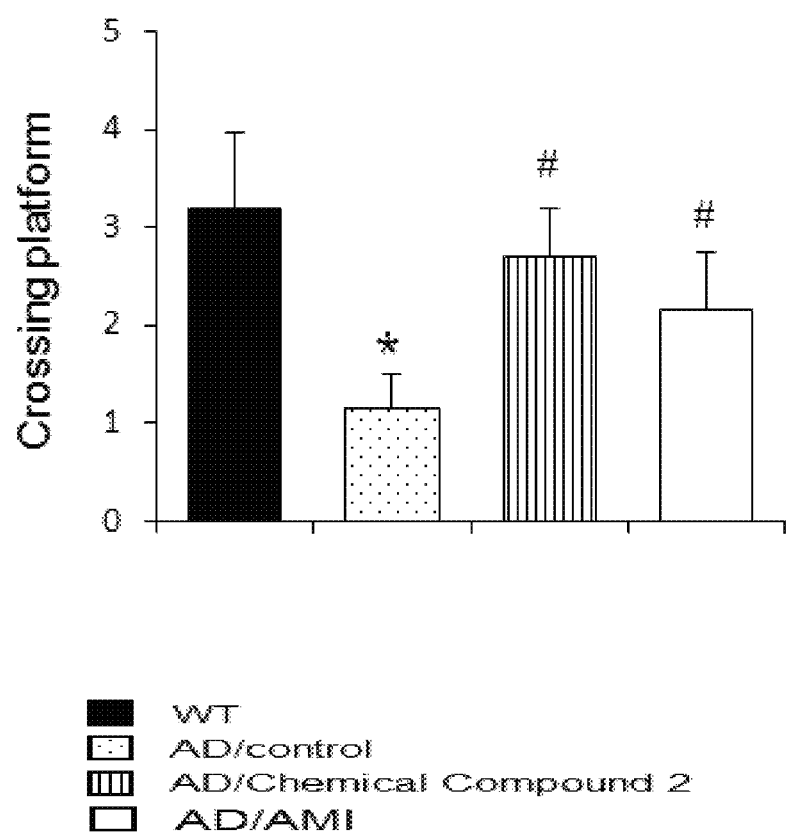
Figure 6D:
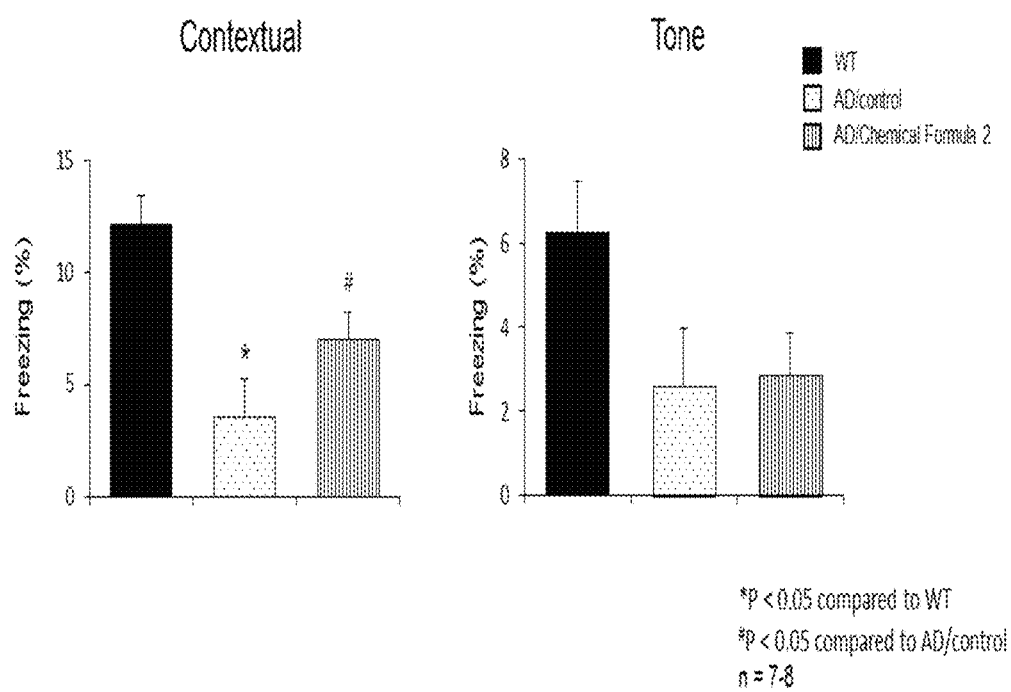
Figure 7A:
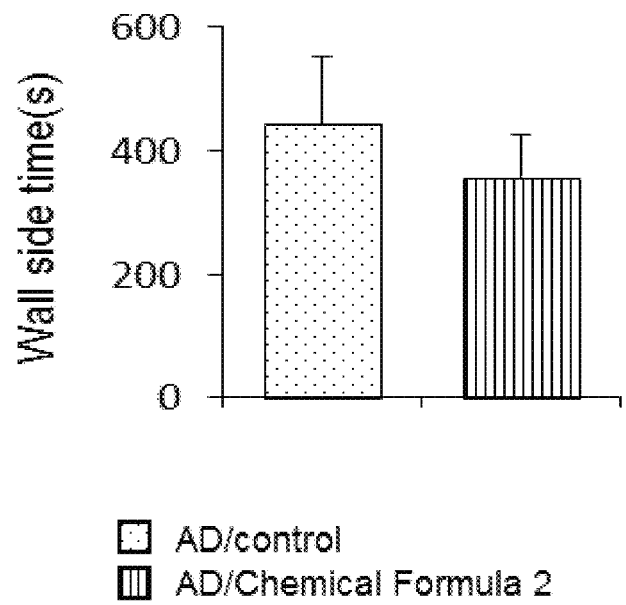
FIGS. 7A through 7I show that the supply of the novel ASM inhibitory compound of the Chemical Formula 2 improved activity and anxiety of APP/PS1 mice (APP/PS1 mice without feeding (n=8) or APP/PS1 mice with feeding (n=7) of the novel ASM inhibitory compound of the Chemical Formula 2).
Figure 7B:
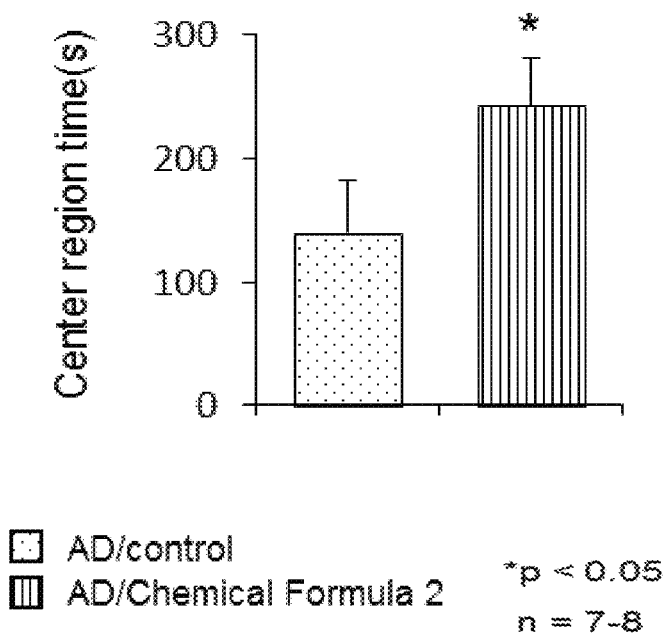
Figure 7C:
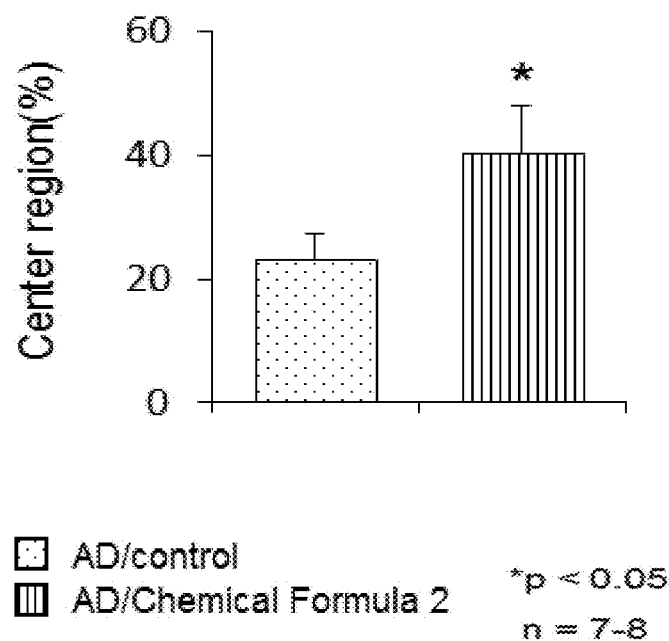
Figure 7D:
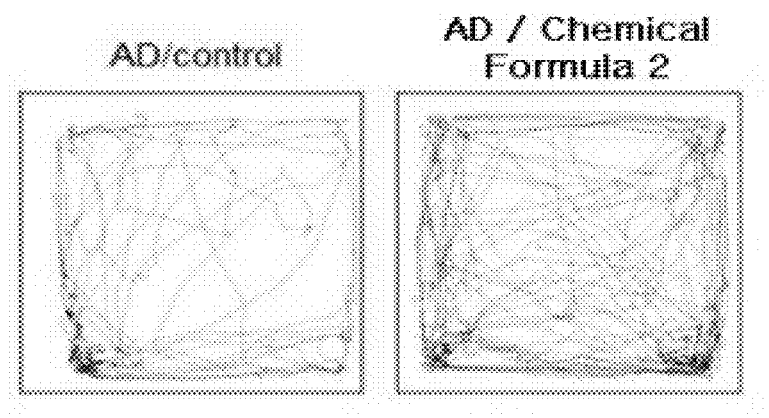
Figure 7E:
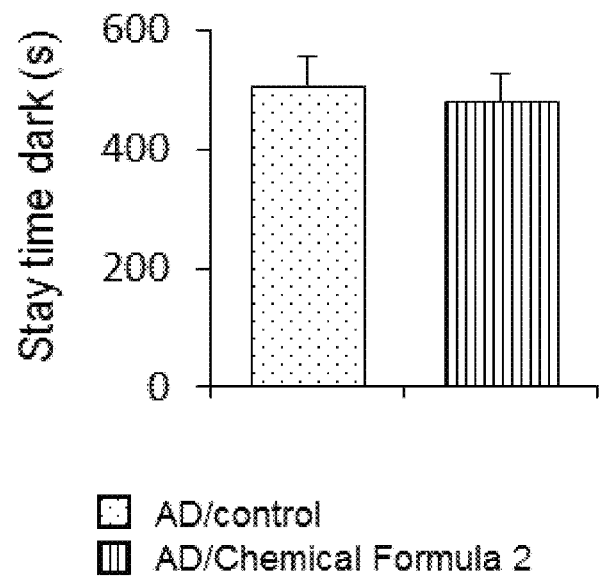
Figure 7F:
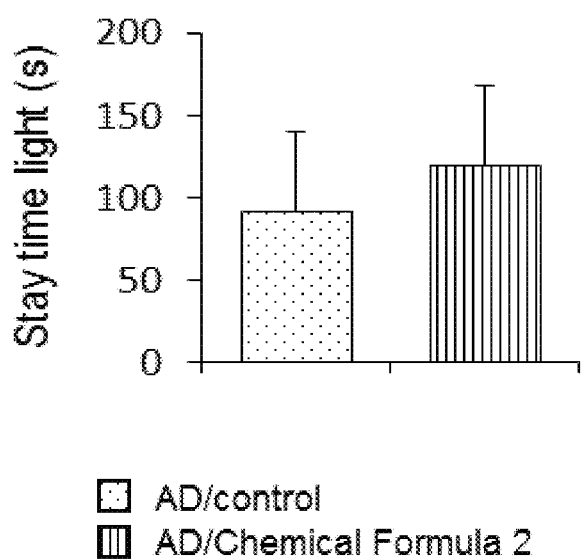
Figure 7G:
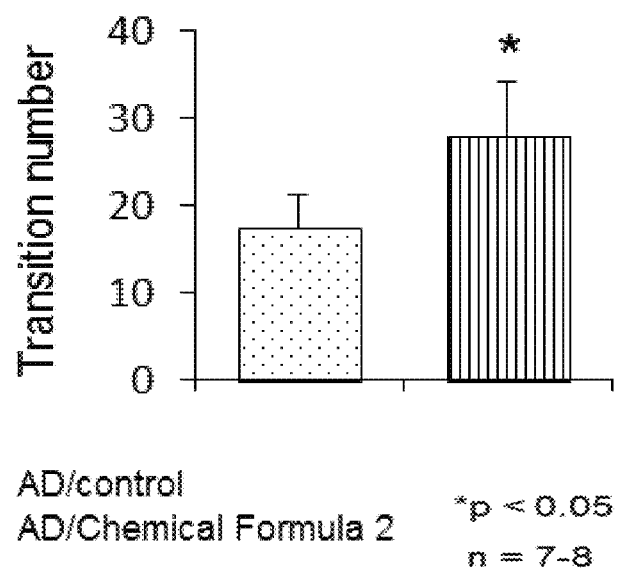
Figure 7H:
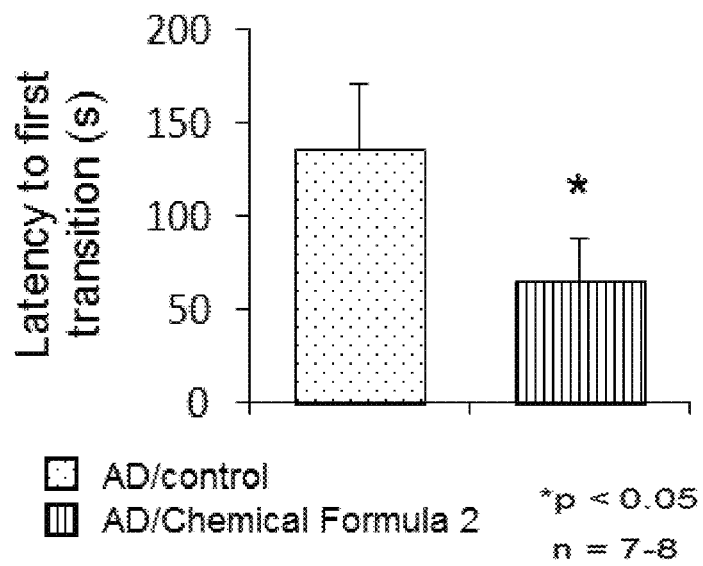
Figure 7I:
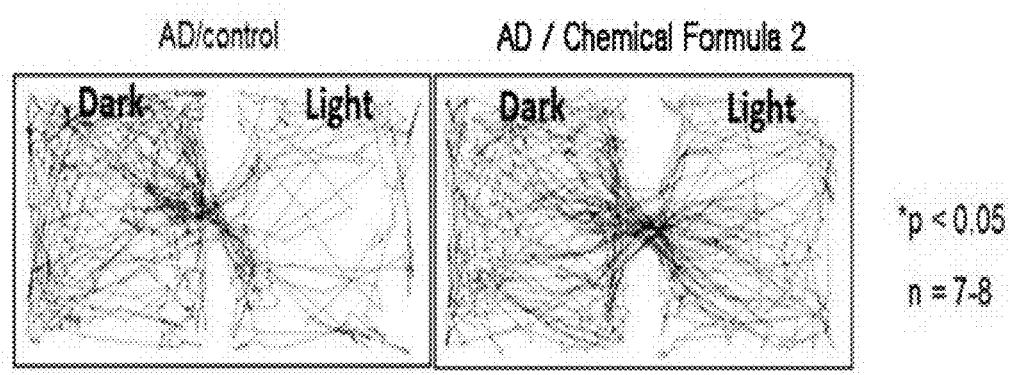

As shown in FIG. 6A, it was found that spatial memory, cognitive and memory formation in APP/PS1 mice were severely disabled, whereas those disability was improved in APP/PS1 mice treated with the novel ASM inhibitory compound of the Chemical Formula 2 or AMI. In particular, it was confirmed that the cognitive improvement in APP/PS1 mice treated with the novel ASM inhibitory compound of the Chemical Formula 2 was more pronounced than in those treated with AMI (See FIGS. 6A-C). Further, it was also found in the fear conditioning test that the novel ASM inhibitory compound of the Chemical Formula 2 exhibited the effect of improving the memory (See FIG. 6D).

In addition, the open field test and Dark & Light test were conducted to evaluate the effect of the novel ASM inhibitory compounds according to the present invention on activity and anxiety.

As shown in FIG. 7, it was confirmed that the activity and anxiety were significantly improved in the APP/PS1 mice treated with the novel ASM inhibitory compound of the Chemical Formula 2, in comparison with the APP/PS1 mice.

Figure 8A:
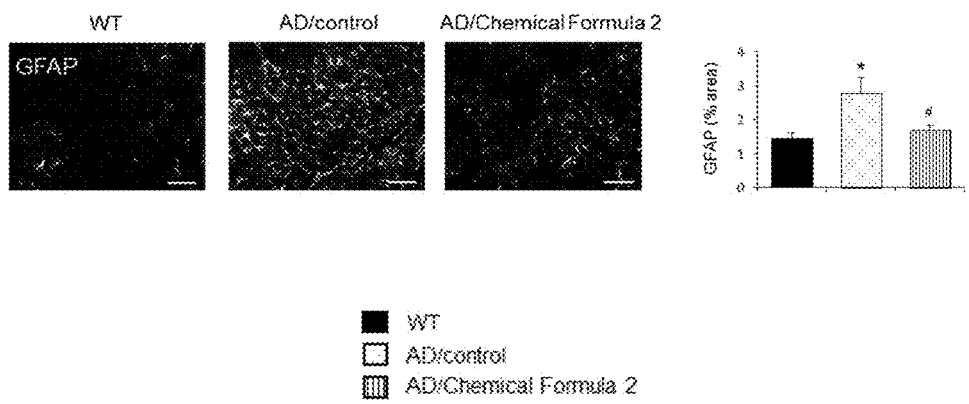
FIGS. 8A and 8B show the results confirming that increased nerve inflammation in APP/PS1 mice (AD) is reduced by feeding the novel ASM inhibitory compound of the Chemical Formula 2 (n=3-4/group).
Figure 8B:
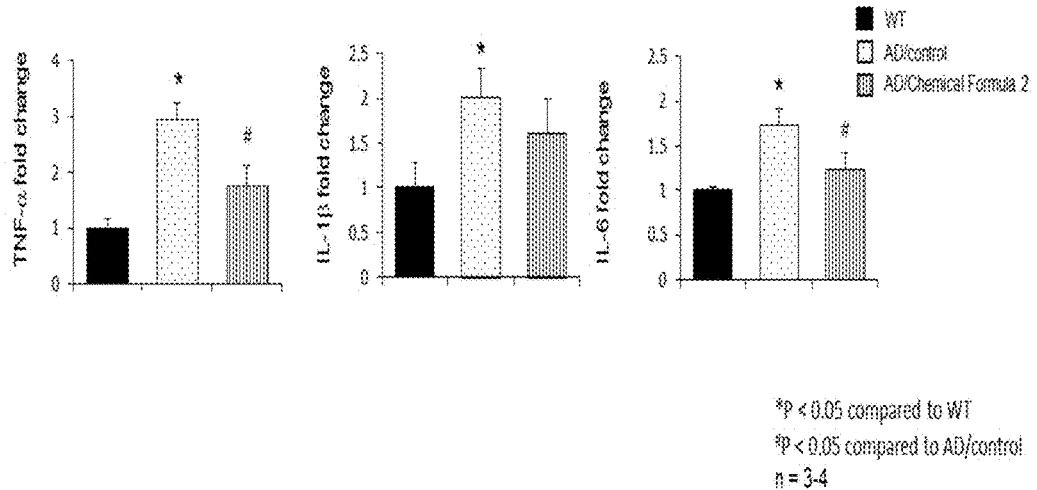

5. Evaluation on the Change of Nerve Inflammation in the APP/PS1 Mice Treated with the Novel ASM Inhibitory Compounds According to the Present Invention In order to determine the effect of the novel ASM inhibitory compounds according to the present invention on the change of nerve inflammation in the APP/PS1 mice, the present inventors observed a change in astrocytes of their brains. In comparison with the APP/PS1 mice, it was confirmed that the activity of astrocytes was significantly decreased in the APP/PS1 mice treated with the novel ASM inhibitory compound of the Chemical Formula 2 (See FIG. 8A). While the APP/PS1 mice showed a markedly increased gene expression of inflammatory cytokines TNF-α, IL-1b and IL-6 compared with wild-type mice, while the expression of such genes was restored to their normal levels in the APP/PS1 mice treated with the novel ASM inhibitory compound of the Chemical Formula 2 (See FIG. 8B).

Through these results, it was verified that the treatment of the novel ASM inhibitory compound of the Chemical Formula 2 controls the nerve inflammation in the brain environment of Alzheimer's disease.

6. Evaluation on the Effect of the Novel ASM Inhibitory Compounds on the Autophagy-Associated Genes in the APP/PS1 Mice In order to verify the mechanism of the ASM inhibitory compound of the Chemical Formula 2 in the autophagy-related pathways upon its administration, the conversion of LC3-I into LC3-II, and the expression levels of Beclin-1, cathepsin D and p62 in the brain tissue samples of the WT mice, APP/PS1 mice, and APP/PS1 mice treated with the ASM inhibitory compound of the Chemical Formula 2 which were 9.5 months old, respectively, were confirmed by Western blotting experiments.

Figure 9:
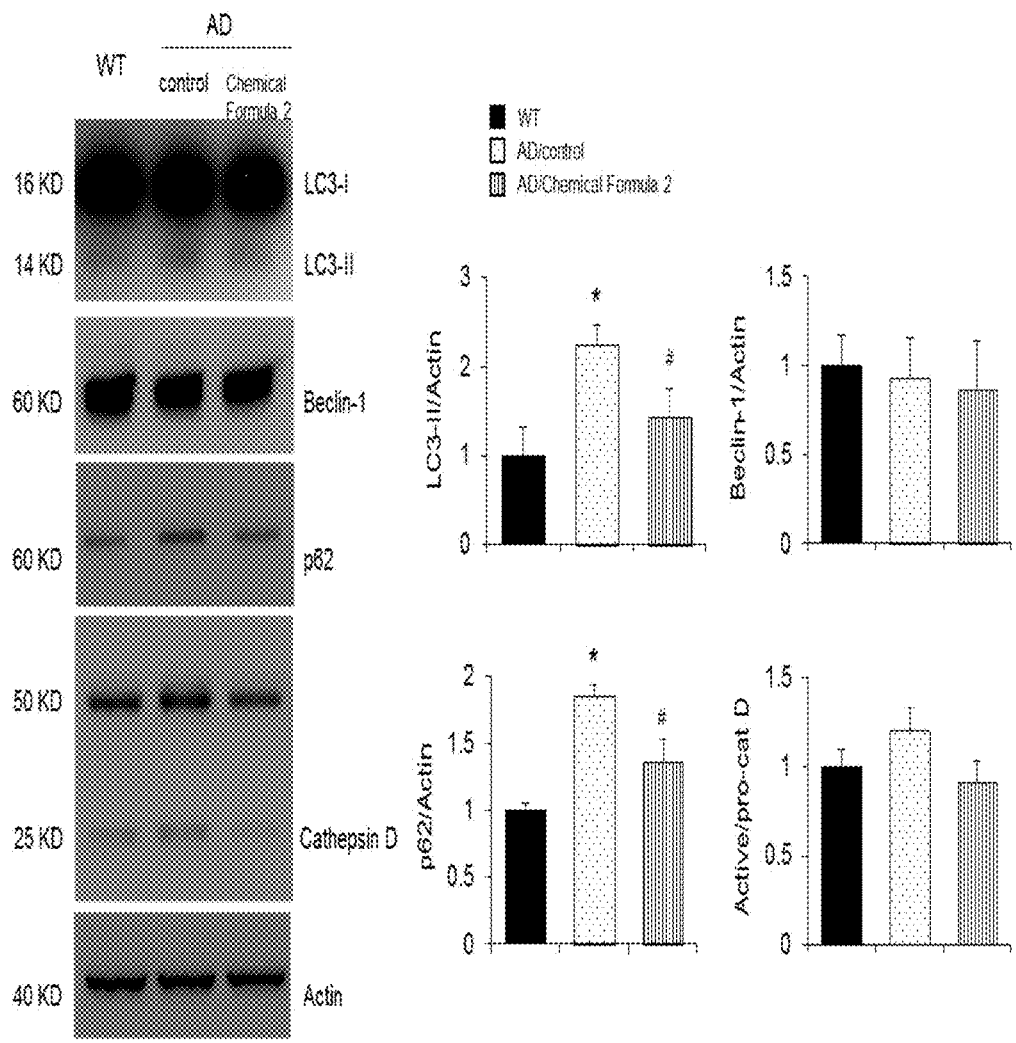
FIG. 9 shows the Western blotting analysis of the expression of autophagy-related proteins in the cerebral cortex of wild type mice (WT) and APP/PS1 mice (AD) that were not fed or fed with the novel ASM inhibitory compound of the Chemical Formula 2 through drinking water, respectively (N=3-4/group).

As shown in FIG. 9, it was found that the APP/PS1 mice showed an increase in the conversion of LC3-I to LC3-II compared with the wild-type (WT) mice, while such a conversion was decreased in the APP/PS1 mice treated with the novel ASM inhibitory compound of the Chemical Formula 2. It was noted that there was little difference in the expression of Beclin-1 among the three test groups.

In addition, it has been known that the expression of cathepsin D (lysosomal hydrolase) and p62, which are an indicator of autophagy turnovers, is increased in Alzheimer's patients and is associated with the pathology of Alzheimer's disease. In comparison with the WT mice, it was found that the APP/PS1 mice showed increased expression levels of p62 and cathepsin D, while such increased expression levels were decreased in the APP/PS1 mice treated with the novel ASM inhibitory compound of the Chemical Formula 2.

In sum, it was verified that the treatment of the novel ASM inhibitory compound of the Chemical Formula 2 in the APP/PS1 mice would reduce the Aβ plaque deposition and inflammation and restore the damaged autophagy. In addition, it was also found that the ASM inhibitory compound of the Chemical Formula 2 would improve learning, memory ability, and activity in the animal models of Alzheimer's disease and reduce anxiety associated with depression, leading to the fact that it can be utilized as a therapeutic agent for treating neurodegenerative diseases including Alzheimer's disease. Further, the present inventors confirmed that the novel ASM inhibitory compounds according to the present invention are excellent in inhibiting ASM activity and treating Alzheimer's disease in comparison with the previously known ASM inhibitors (such as AMI and FTY720).

In comparison with conventional ASM inhibitor agents, the novel ASM inhibitory compounds of the Chemical Formula 1 according to the present invention are excellent in therapeutic effects such as inhibiting ASM activity, reducing Aβ plaques in the brain environment of Alzheimer's disease, recovering the damages by autophagy, and ameliorating nerve inflammation. Hence, the compounds of the present invention possess the excellent industrial applicability since they can be used in the development of agents for preventing or treating a neurodegenerative disease including Alzheimer's disease and depression.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for treating a neurodegenerative disease or depression, the method comprising administering to a subject in need thereof an effective amount of a compound of the following Chemical Formula 1 or a pharmaceutically acceptable salt thereof:

[Chemical Formula 1]

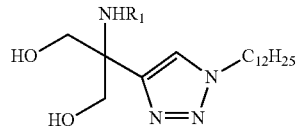

wherein $R_1$ is hydrogen or an acetyl group.

2. The method of claim 1, wherein the compound of the Chemical Formula 1 exerts an effect of inhibiting the activity of ASM (acid sphingomyelinase).

3. The method of claim 1, wherein the neurodegenerative disease is at least one selected from the group consisting of Alzheimer's disease, Parkinson's disease, progressive supranuclear palsy, multiple system atrophy, olivopontocerebellar atrophy (OPCA), Shy-Drager syndrome, striatonigral degeneration, Huntington disease, amyotrophic lateral sclerosis (ALS), essential tremor, cortico-basal ganglionic degeneration, diffuse Lewy body disease, Parkinson-ALS-dementia complex of Guam, Pick's disease, cerebral ischemia and cerebral infarction.

* * * * *